United States Patent
Midha et al.

(10) Patent No.: US 12,233,139 B2
(45) Date of Patent: *Feb. 25, 2025

(54) ORAL CARE COMPOSITIONS CONTAINING A GEL NETWORK PHASE

(71) Applicant: The Procter & Gamble Company, Cincinnati, OH (US)

(72) Inventors: Sanjeev Midha, Mason, OH (US); Lawrence Edward Dolan, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 149 days.

This patent is subject to a terminal disclaimer.

(21) Appl. No.: 18/074,838

(22) Filed: Dec. 5, 2022

(65) Prior Publication Data

US 2023/0104890 A1 Apr. 6, 2023

Related U.S. Application Data

(63) Continuation of application No. 17/000,393, filed on Aug. 24, 2020, now Pat. No. 11,517,509, which is a continuation of application No. 15/475,170, filed on Mar. 31, 2017, now abandoned.

(60) Provisional application No. 62/317,413, filed on Apr. 1, 2016.

(51) Int. Cl.
| | | |
|---|---|---|
| A61K 8/21 | (2006.01) | |
| A61K 8/00 | (2006.01) | |
| A61K 8/02 | (2006.01) | |
| A61K 8/04 | (2006.01) | |
| A61K 8/18 | (2006.01) | |
| A61K 8/19 | (2006.01) | |
| A61K 8/22 | (2006.01) | |
| A61K 8/24 | (2006.01) | |
| A61K 8/25 | (2006.01) | |
| A61K 8/34 | (2006.01) | |
| A61K 8/46 | (2006.01) | |
| A61K 8/73 | (2006.01) | |
| A61K 8/81 | (2006.01) | |
| A61Q 11/00 | (2006.01) | |

(52) U.S. Cl.
CPC ............ *A61K 8/0216* (2013.01); *A61K 8/042* (2013.01); *A61K 8/19* (2013.01); *A61K 8/21* (2013.01); *A61K 8/22* (2013.01); *A61K 8/24* (2013.01); *A61K 8/25* (2013.01); *A61K 8/342* (2013.01); *A61K 8/463* (2013.01); *A61K 8/73* (2013.01); *A61K 8/8158* (2013.01); *A61Q 11/00* (2013.01); *A61K 2800/28* (2013.01); *A61K 2800/412* (2013.01); *A61K 2800/48* (2013.01)

(58) Field of Classification Search
CPC .... A61Q 11/00; A61K 8/042; A61K 2800/48; A61K 2800/92; A61K 8/21
See application file for complete search history.

(56) References Cited

U.S. PATENT DOCUMENTS

| | | |
|---|---|---|
| 1,370,665 A | 3/1921 | Harlan |
| 1,433,167 A | 10/1922 | Worden |
| 1,581,469 A | 4/1926 | Oskin |
| 1,673,590 A | 6/1928 | Redheffer |
| 1,836,800 A | 12/1931 | Hope |
| 1,950,769 A | 3/1934 | Baar |
| 1,978,455 A | 10/1934 | Geerlings |
| 2,300,512 A | 11/1942 | Landau |
| 2,632,446 A | 3/1953 | Rosenzweig |
| 2,818,872 A | 1/1958 | Wang |
| 3,045,343 A | 7/1962 | Baruch |
| 3,078,017 A | 2/1963 | Karlheinz et al. |
| 3,488,764 A | 1/1970 | Welsh |
| 3,492,723 A | 2/1970 | Mollica et al. |
| 3,593,416 A | 7/1971 | Edson |
| 3,777,396 A | 12/1973 | Simonetti |
| 3,985,146 A | 10/1976 | Albach |
| 4,020,154 A | 4/1977 | Perla |
| 4,129,942 A | 12/1978 | Denizman |
| 4,433,483 A | 2/1984 | Lazarus |
| 4,446,619 A | 5/1984 | Jacobson |
| 4,470,521 A | 9/1984 | Scammell |
| D281,282 S | 11/1985 | Lazarus |
| 4,562,643 A | 1/1986 | Cataudella |
| 4,573,266 A | 3/1986 | Jacobson |
| 4,625,402 A | 12/1986 | Kavoussi |
| 4,635,361 A | 1/1987 | DeMars |
| 4,666,517 A | 5/1987 | Bakar |
| 4,696,106 A | 9/1987 | Cross et al. |
| 4,716,652 A | 1/1988 | Cataudella |
| D294,661 S | 3/1988 | Kang |
| 4,753,006 A | 6/1988 | Howe |
| 4,791,723 A | 12/1988 | Jacobson |

(Continued)

FOREIGN PATENT DOCUMENTS

| | | |
|---|---|---|
| AU | 2002318865 A1 | 6/2004 |
| CA | 2570867 C | 7/2008 |

(Continued)

OTHER PUBLICATIONS

14275M International Search Report and Written Opinion for PCT/US2017/025236 dated Jun. 20, 2017, 10 pgs.
All Office Actions, U.S. Appl. No. 29/601,000, filed on Apr. 18, 2017.
All Office Actions, U.S. Appl. No. 29/672,275, filed on Dec. 4, 2018.

(Continued)

*Primary Examiner* — Tracy Liu
(74) *Attorney, Agent, or Firm* — John G. Powell

(57) ABSTRACT

An oral care composition containing a gel phase, an abrasive, and a fluoride source. The gel network phase contains a fatty amphiphile and phase separation is not visually perceptible in the oral care composition.

16 Claims, No Drawings

(56) References Cited

U.S. PATENT DOCUMENTS

| | | |
|---|---|---|
| 4,809,432 A | 3/1989 | Schauble |
| 4,813,138 A | 3/1989 | Chen |
| 4,868,982 A | 9/1989 | McComas |
| 4,881,323 A | 11/1989 | McGaughan |
| D306,496 S | 3/1990 | Newberry |
| D309,036 S | 7/1990 | Cheng |
| D310,271 S | 8/1990 | Jacobson |
| D311,784 S | 10/1990 | Schwartz |
| 4,970,784 A | 11/1990 | Althaus et al. |
| 4,974,319 A | 12/1990 | Maguire, Jr. et al. |
| D317,715 S | 6/1991 | Bauwens |
| 5,070,611 A | 12/1991 | Derin et al. |
| 5,083,336 A | 1/1992 | Atsumi et al. |
| 5,093,112 A | 3/1992 | Birtwistle et al. |
| 5,133,131 A | 7/1992 | Hoffman |
| 5,269,062 A | 12/1993 | Dallaire et al. |
| 5,274,922 A | 1/1994 | Elliott |
| 5,287,624 A | 2/1994 | Mondo et al. |
| 5,318,203 A | 6/1994 | Iaia et al. |
| 5,403,534 A | 4/1995 | Kim |
| 5,512,278 A | 4/1996 | Mundschenk |
| 5,547,091 A | 8/1996 | Neveras et al. |
| D374,615 S | 10/1996 | Kani |
| 5,579,580 A | 12/1996 | Althaus et al. |
| 5,655,302 A | 8/1997 | Mroczka |
| 5,661,907 A | 9/1997 | Apprille, Jr. |
| 5,687,485 A | 11/1997 | Shurtleff et al. |
| D392,879 S | 3/1998 | Couey |
| 5,819,413 A | 10/1998 | Kerbrat |
| 5,855,066 A | 1/1999 | Manger |
| 5,983,500 A | 11/1999 | Da Silva |
| 6,053,184 A | 4/2000 | Devone |
| D426,917 S | 6/2000 | Hokanson |
| 6,082,006 A | 7/2000 | Cahan |
| 6,164,290 A | 12/2000 | Andrews |
| D440,494 S | 4/2001 | Sagel et al. |
| 6,370,783 B1 | 4/2002 | Bozikis et al. |
| 6,434,828 B1 | 8/2002 | Andrews |
| 6,550,148 B2 | 4/2003 | Cecil |
| 6,665,937 B2 | 12/2003 | Fuerst et al. |
| D489,485 S | 5/2004 | Leventhal |
| 6,754,958 B2 | 6/2004 | Haws et al. |
| D502,099 S | 2/2005 | Lovell |
| 6,871,679 B2 | 3/2005 | Last |
| 6,910,274 B1 | 6/2005 | Pennella et al. |
| 6,986,207 B2 | 1/2006 | Selek |
| 7,051,439 B2 | 5/2006 | Tomasetti |
| D525,526 S | 7/2006 | Abbott et al. |
| 7,086,160 B2 | 8/2006 | Coffin et al. |
| 7,121,754 B2 | 10/2006 | Bressler et al. |
| 7,137,203 B2 | 11/2006 | Bressler et al. |
| 7,178,241 B1 | 2/2007 | Cummings et al. |
| 7,234,239 B2 | 6/2007 | Saito et al. |
| D567,442 S | 4/2008 | Mcmullan |
| D602,634 S | 10/2009 | Cataudella |
| D615,417 S | 5/2010 | Fallat, II et al. |
| 7,788,809 B2 | 9/2010 | Tomassetti |
| 7,814,661 B2 | 10/2010 | Tomassetti |
| 7,818,883 B2 | 10/2010 | Lax |
| D626,428 S | 11/2010 | Fallat, II et al. |
| D626,860 S | 11/2010 | Oates et al. |
| 8,028,417 B1 | 10/2011 | Hosseini et al. |
| 8,033,023 B2 | 10/2011 | Johnson et al. |
| D660,516 S | 5/2012 | Christie |
| D662,416 S | 6/2012 | Dziersk et al. |
| 8,261,451 B2 | 9/2012 | Macove |
| D669,220 S | 10/2012 | Otsuka |
| D675,377 S | 1/2013 | Boulanger |
| 8,365,416 B2 | 2/2013 | Rockell et al. |
| 8,474,354 B2 | 7/2013 | Horton |
| 8,510,957 B2 | 8/2013 | Wain et al. |
| D693,237 S | 11/2013 | Bates et al. |
| D696,461 S | 12/2013 | Prat-Pfister |
| 8,607,458 B2 | 12/2013 | Hosseini et al. |
| 8,863,968 B2 | 10/2014 | Giusti |
| 8,931,177 B2 | 1/2015 | Wain et al. |
| 9,005,585 B2 | 4/2015 | Deckner |
| 9,120,602 B2 | 9/2015 | Lagace |
| D742,228 S | 11/2015 | Dyer et al. |
| 9,221,185 B2 | 12/2015 | Walker, Jr. |
| D751,908 S | 3/2016 | Lee et al. |
| D752,987 S | 4/2016 | Dyer et al. |
| D756,235 S | 5/2016 | Dyer et al. |
| 9,434,079 B2 | 9/2016 | Worrick, III |
| 9,434,081 B2 | 9/2016 | Kumar |
| 9,579,809 B2 | 2/2017 | Hawes |
| 9,694,503 B2 | 7/2017 | Papadopoulos-papageorgis et al. |
| 9,833,916 B2 | 12/2017 | Shorey et al. |
| 9,908,689 B2 | 3/2018 | Schulz et al. |
| D839,477 S | 1/2019 | Hodgson |
| 10,219,988 B2 | 3/2019 | Midha et al. |
| 10,232,521 B2 | 3/2019 | Wain et al. |
| D873,150 S | 1/2020 | Renard |
| D882,873 S | 4/2020 | Goeder et al. |
| D887,641 S | 6/2020 | Ramm et al. |
| D887,642 S | 6/2020 | Hodgson |
| D913,593 S | 3/2021 | Hodgson |
| D977,196 S | 1/2023 | Goeder |
| D987,184 S | 5/2023 | Mcgarry et al. |
| 2003/0044313 A1 | 3/2003 | Lee |
| 2003/0196328 A1 | 10/2003 | Andino et al. |
| 2004/0016126 A1 | 1/2004 | deBlois |
| 2004/0172831 A1 | 9/2004 | Paas et al. |
| 2004/0177518 A1 | 9/2004 | Leventhal |
| 2004/0177519 A1 | 9/2004 | Tomassetti et al. |
| 2004/0206775 A1 | 10/2004 | Holmes |
| 2004/0226178 A1 | 11/2004 | Lukan et al. |
| 2005/0022386 A1 | 2/2005 | Macove |
| 2005/0120560 A1 | 6/2005 | Franzini et al. |
| 2005/0126008 A1 | 6/2005 | Pennella |
| 2005/0132574 A1 | 6/2005 | Tomassetti |
| 2005/0198830 A1 | 9/2005 | Walker |
| 2005/0198840 A1 | 9/2005 | Worrick, III et al. |
| 2005/0246906 A1 | 11/2005 | Greene |
| 2006/0034784 A1 | 2/2006 | Cahen et al. |
| 2006/0150386 A1 | 7/2006 | Wanli et al. |
| 2006/0210491 A1 | 9/2006 | Behan |
| 2006/0272154 A1 | 12/2006 | Brevard |
| 2007/0017097 A1 | 1/2007 | Scheindel |
| 2007/0050983 A1 | 3/2007 | Schnak et al. |
| 2007/0251106 A1 | 11/2007 | Gladstone |
| 2008/0022529 A1 | 1/2008 | Gray |
| 2008/0034591 A1 | 2/2008 | Fung |
| 2008/0081023 A1 | 4/2008 | Deckner |
| 2008/0134525 A1 | 6/2008 | Gratsias et al. |
| 2008/0201966 A1 | 8/2008 | Psimadas et al. |
| 2008/0307653 A1 | 12/2008 | Wattam |
| 2009/0038737 A1 | 2/2009 | Previty et al. |
| 2009/0113730 A1 | 5/2009 | Psimadas et al. |
| 2009/0126197 A1 | 5/2009 | Tomassetti |
| 2009/0246151 A1 | 10/2009 | Leblanc |
| 2009/0249628 A1 | 10/2009 | Hosseini |
| 2009/0297460 A1 | 12/2009 | Lamb et al. |
| 2010/0077622 A1 | 4/2010 | Schulz |
| 2010/0175261 A1 | 7/2010 | Lax |
| 2010/0175270 A1 | 7/2010 | Psimadas et al. |
| 2010/0205808 A1 | 8/2010 | King |
| 2010/0236071 A1 | 9/2010 | Szczepanowski et al. |
| 2010/0236072 A1 | 9/2010 | Szczepanowski |
| 2011/0023310 A1 | 2/2011 | Psimadas |
| 2011/0036371 A1 | 2/2011 | Marroncles et al. |
| 2011/0146080 A1 | 6/2011 | Pauw |
| 2011/0162209 A1 | 7/2011 | Wain |
| 2011/0180567 A1 | 7/2011 | Bender et al. |
| 2011/0197446 A1 | 8/2011 | Macove |
| 2011/0203112 A1 | 8/2011 | Lax |
| 2012/0023762 A1 | 2/2012 | Furuta |
| 2012/0094051 A1 | 4/2012 | Chang |
| 2012/0096718 A1 | 4/2012 | Howell et al. |
| 2012/0103362 A1 | 5/2012 | Nowacek |
| 2012/0198698 A1 | 8/2012 | Szczepanowski et al. |
| 2012/0233868 A1 | 9/2012 | Bridges et al. |
| 2012/0255185 A1 | 10/2012 | Patel et al. |
| 2012/0291290 A1 | 11/2012 | Fishman et al. |

(56) References Cited

U.S. PATENT DOCUMENTS

| | | |
|---|---|---|
| 2013/0061481 A1 | 3/2013 | Cooney |
| 2013/0081276 A1 | 4/2013 | Wain |
| 2013/0081291 A1 | 4/2013 | Wain |
| 2013/0145624 A1 | 6/2013 | Jessemey et al. |
| 2013/0145625 A1 | 6/2013 | Xu et al. |
| 2013/0160305 A1 | 6/2013 | Howell |
| 2013/0195774 A1 | 8/2013 | Leblanc |
| 2013/0247381 A1 | 9/2013 | Blaustein et al. |
| 2013/0255088 A1 | 10/2013 | Christie et al. |
| 2013/0341354 A1 | 12/2013 | Archer |
| 2014/0083265 A1 | 3/2014 | Provost |
| 2014/0127145 A1 | 5/2014 | Deckner |
| 2014/0216215 A1 | 8/2014 | Hosseini et al. |
| 2014/0290066 A1 | 10/2014 | Woolfson et al. |
| 2014/0308322 A1 | 10/2014 | Midha et al. |
| 2014/0336308 A1 | 11/2014 | Mateu et al. |
| 2015/0023890 A1 | 1/2015 | Joziak et al. |
| 2015/0075012 A1 | 3/2015 | Opinel |
| 2015/0121703 A1 | 5/2015 | Bridges et al. |
| 2015/0197021 A1 | 7/2015 | Hodgson |
| 2015/0239138 A1 | 8/2015 | Kurzet et al. |
| 2015/0259097 A1 | 9/2015 | O'hare |
| 2015/0266191 A1 | 9/2015 | Maimone et al. |
| 2015/0328787 A1 | 11/2015 | Ortins |
| 2016/0167242 A1 | 6/2016 | Noh et al. |
| 2016/0250765 A1 | 9/2016 | Gratsias et al. |
| 2016/0250766 A1 | 9/2016 | Gratsias |
| 2017/0001320 A1 | 1/2017 | Hodgson et al. |
| 2017/0001321 A1 | 1/2017 | Shorey et al. |
| 2017/0036361 A1 | 2/2017 | Bushell |
| 2017/0066148 A1 | 3/2017 | Hodgson et al. |
| 2017/0112002 A1 | 4/2017 | Behrendt |
| 2017/0264036 A1 | 9/2017 | Broemse |
| 2017/0267827 A1 | 9/2017 | Rowan |
| 2017/0281476 A1 | 10/2017 | Midha et al. |
| 2017/0281482 A1 | 10/2017 | Midha |
| 2017/0281486 A1 | 10/2017 | Midha |
| 2017/0282390 A1 | 10/2017 | Hodgson |
| 2017/0326743 A1 | 11/2017 | Hodgson |
| 2017/0368702 A1 | 12/2017 | Wain et al. |
| 2018/0115339 A1 | 4/2018 | Altschul et al. |
| 2018/0168052 A1 | 6/2018 | Behrendt et al. |
| 2018/0194027 A1 | 7/2018 | Tews et al. |
| 2018/0297220 A1 | 10/2018 | Hodgson |
| 2018/0297221 A1 | 10/2018 | Hodgson |
| 2018/0297222 A1 | 10/2018 | Hodgson |
| 2018/0297223 A1 | 10/2018 | Hodgson |
| 2018/0297225 A1 | 10/2018 | Hodgson |
| 2019/0077033 A1 | 3/2019 | Hodgson |
| 2019/0365078 A1 | 12/2019 | Bourque |
| 2020/0047361 A1 | 2/2020 | Valcov |
| 2020/0130209 A1 | 4/2020 | Maurer et al. |
| 2020/0254639 A1 | 8/2020 | Bridges et al. |
| 2020/0383882 A1 | 12/2020 | Midha et al. |
| 2021/0283791 A1 | 9/2021 | Siegmann et al. |
| 2022/0001559 A1 | 1/2022 | Hiller et al. |
| 2023/0028003 A1 | 1/2023 | Bridges et al. |

FOREIGN PATENT DOCUMENTS

| | | |
|---|---|---|
| CN | 2044927 U | 9/1989 |
| CN | 2130660 Y | 4/1993 |
| CN | 1802114 A | 7/2006 |
| CN | 101115595 A | 1/2008 |
| CN | 202507311 U | 10/2012 |
| DE | 29711818 U1 | 10/1997 |
| EP | 0123765 A1 | 11/1984 |
| EP | 0101767 B1 | 4/1988 |
| EP | 0348560 A1 | 1/1990 |
| JP | 3622288 B2 | 12/2004 |
| KR | 20080031335 A | 4/2008 |
| WO | 97018065 A1 | 5/1997 |
| WO | 2003006217 A1 | 1/2003 |
| WO | 2007136381 A1 | 11/2007 |
| WO | 2009019521 A4 | 4/2009 |
| WO | 2011053877 A2 | 5/2011 |
| WO | 2014030990 A1 | 2/2014 |

OTHER PUBLICATIONS

All Office Actions, U.S. Appl. No. 29/735,584, filed on May 22, 2020.
All Office Actions, U.S. Appl. No. 15/475,170, filed on Mar. 31, 2017.
All Office Actions; U.S. Appl. No. 15/951,287, filed on Apr. 12, 2018.
All Office Actions; U.S. Appl. No. 15/951,273, filed on Apr. 12, 2018.
All Office Actions; U.S. Appl. No. 15/951,312, filed on Apr. 12, 2018.
All Office Actions; U.S. Appl. No. 15/951,323, filed on Apr. 12, 2018.
All Office Actions; U.S. Appl. No. 15/951,339, filed on Apr. 12, 2018.
All Office Actions; U.S. Appl. No. 17/000,393, filed on Aug. 24, 2020.
All Office Actions; U.S. Appl. No. 29/770,328, filed on Feb. 11, 2021.
CAB Surface Roughness Conversion Chart, Aug. 2014, 1 page.
Upmold Surface Roughness Technical Data, Sep. 2018, 1 page.
U.S. Appl. No. 29/770,328, filed Feb. 11, 2021, Matthew James Hodgson.

ORAL CARE COMPOSITIONS CONTAINING A GEL NETWORK PHASE

FIELD OF THE INVENTION

The present invention relates to an oral care composition. More particularly a toothpaste composition containing a gel network phase and a cold dispersible fatty amphiphile.

BACKGROUND OF THE INVENTION

Oral care compositions, including toothpaste compositions, can contain fluoride salts, peroxide, abrasives, and flavors to clean teeth, freshen breath, and maintain the aesthetics and health of the oral cavity, including the teeth and gums.

Formulating toothpaste compositions with the proper rheology can be very challenging. The composition must not be too thick so it can easily dispense out of a tube but thick enough to stand up on a toothbrush without sinking into the bristles. The viscosity of the oral composition must remain stable over time as not to continue to thicken so the oral composition remains easy to dispense during the shelf life. Once dispensed from a container, the oral composition should not be stringy or sticky as to be messy for a consumer to use. The oral composition must also easily disperse once in the mouth and foam. It is also desired that the oral composition not stick to a sink or leave difficult to remove residue. In addition to balancing the viscosity and shear thinning to formulate acceptable rheology, the oral composition must also keep active ingredients including fluoride salts, peroxides, and/or potassium nitrate stable and available for at least the shelf life of the product.

One way to improve toothpaste rheology and stability is to include a gel network phase as a structurant. The gel network phase can include a fatty amphiphile, such as a fatty alcohol, and a secondary surfactant. Including a gel network phase can also provide a unique brushing experience. For instance, toothpaste that contains a gel network phase can have excellent foaming and the foam may not easily break down during brushing, even when it is used with an electric toothbrush. Also, some commercially available toothpastes can feel harsh and can irritate a user's mouth, however, toothpastes containing gel networks can feel smooth and are generally non-irritating. Additionally, after brushing, the mouth not only feels fresh and clean, but a user's teeth can feel especially smooth and the smoothness can persist throughout the day because the amount of biofilm that builds on the teeth between brushings can be significantly reduced.

However, it can be particularly difficult to formulate stable toothpaste compositions with a gel network phase, especially gel network toothpaste compositions that limit the amount of fatty alcohol in the toothpaste, since fatty alcohols may contribute to unacceptable aesthetics such as suboptimum flavor display, taste, and foaming and some consumers noticed greasy feeling in the mouth and lips after brushing, As such, there is a need for an improved oral care composition that contain a gel network and have consumer acceptable aesthetics.

SUMMARY OF THE INVENTION

An oral care composition comprising: (a) a gel network phase comprising a fatty amphiphile; (b) an abrasive; and (c) a fluoride ion source selected from the group consisting of stannous fluoride, sodium fluoride, potassium fluoride, amine fluoride, sodium monofluorophosphate, indium fluoride, amine fluoride, and combinations thereof; wherein the oral care composition comprises from about 3% to about 17% fatty amphiphile; wherein phase separation is not visually perceptible as determined by the phase separation method.

An oral care composition comprising: (a) a gel network phase comprising a fatty amphiphile; (b) from about 0.01% to about 3% thickening material selected from the group consisting of carboxyvinyl polymers, carrageenan, hydroxyethyl cellulose, water soluble salts of cellulose ethers, gum karaya, xanthan gum, gum arabic, gum tragacanth, magnesium aluminum silicate, finely divided silica, and combinations thereof; (c) an abrasive; and (d) a fluoride ion source selected from the group consisting of stannous fluoride, sodium fluoride, potassium fluoride, amine fluoride, sodium monofluorophosphate, indium fluoride, amine fluorides, and combinations thereof; wherein the oral care composition comprises less than about 10% fatty amphiphile; and wherein phase separation is not visually perceptible as determined by the phase separation method.

A method for making an oral care composition comprising the steps of: (a) combining water and a fatty amphiphile; (b) adding a fluoride ion source and/or an abrasive; (c) adding a secondary surfactant; (d) mixing until the composition is substantially homogeneous; (e) deaerating until the composition is substantially free of air; wherein a gel network is formed and wherein the composition is not heated above about 30° C.

DETAILED DESCRIPTION OF THE INVENTION

Oral care compositions can include fluoride, peroxide, potassium nitrate, abrasives, flavors, peroxides, and other ingredients to provide benefits like reducing plaque and tartar, reducing pain from sensitive teeth, preventing cavities, preventing and reversing gingivitis, building protection against sensitivity, freshening bad breath, and whitening teeth.

It can be particularly desirable to formulate a toothpaste that includes a gel network phase, which can provide improved rheology and stability and a unique brushing experience. During brushing, the gel network can help the toothpaste feel smooth and non-irritating and can also provide excellent foaming. Furthermore, after brushing teeth can feel especially smooth and the amount of biofilm that accumulates on a user's teeth between brushings can be significantly reduced.

However, it can be difficult to formulate an acceptable toothpaste composition that contains a gel network phase because the gel network phase can include a high level of fatty amphiphile. If the level of fatty amphiphile is too high, the toothpaste may have undesirable aesthetics, including suboptimal taste and flavor display and a greasy feeling in the oral cavity and on the lips. If, the fatty alcohols in the toothpaste are too high, some consumers have mentioned that their lips feel like they are covered in lard during and after use.

The toothpaste composition can contain a gel network which can include a cold dispersible fatty amphiphile, a fluoride ion source, and an abrasive. The toothpaste can be phase stable and can contain less than about 14% fatty amphiphiles. The toothpaste can be phase stable and can contain a gel network phase, which can include a cold dispersible fatty amphiphile and the composition can also contain carrageenan and the composition can contain less than about 5% fatty amphiphiles.

The toothpaste composition can be phase stable and phase separation is not visually perceptible, as determined by the Phase Separation Method, described hereafter.

The toothpaste composition may not have a visually perceptible phase separation. The term "visually perceptible" as used herein means that a human viewer can visually discern a phase separation with the unaided eye (excepting standard corrective lenses adapted to compensate for nearsightedness, farsightedness, or stigmatism, or other corrected vision) in lighting at least equal to the illumination of a standard 100 watt incandescent white light bulb at a distance of approximately 18 inches.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. (i.e. room temperature) unless otherwise specified.

The composition can contain, consist of, or consist essentially of, the essential elements and limitations of the invention described herein, as well as any additional or optional ingredients, components, or limitations described herein or otherwise useful in oral care compositions.

As used herein, the word "include," and its variants, are intended to be non-limiting, such that recitation of items in a list is not to the exclusion of other like items that may also be useful in the materials, compositions, devices, and methods of this invention.

As used herein, the articles "a" and "an" are understood to mean one or more of the material that is claimed or described, for example, "an abrasive" or "a surfactant".

As used herein, the word "or" when used as a connector of two or more elements is meant to include the elements individually and in combination; for example X or Y, means X or Y or both.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include toothpaste, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dispenser", as used herein, means any pump, tube, or container suitable for dispensing compositions such as toothpastes.

The term "effective amount or "effective level" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. In one embodiment, "effective amount" means at least 0.01% of the material, by weight of the composition, alternatively at least 0.1%. An "effective level" of potassium nitrate can be about 5%.

The term "secondary surfactant" as used herein means a surfactant other than a fatty amphiphile. Various types of suitable surfactants are listed below. There may be more than one secondary surfactants. There can be at least one secondary surfactant in the gel network phase and there may be another surfactant in the oral carrier phase.

The term "teeth", as used herein, refers to natural teeth as well as artificial teeth or dental prosthesis.

The term "toothpaste", as used herein, includes tooth or subgingival paste, gel, or liquid formulations unless otherwise specified. The toothpaste composition may be a single phase composition or may be a combination of two or more separate toothpaste compositions. The toothpaste composition may be in any desired form, such as deep striped, surface striped, multilayered, having a gel surrounding a paste, or any combination thereof. Each toothpaste composition in a toothpaste comprising two or more separate toothpaste compositions may be contained in a physically separated compartment of a dispenser and dispensed side-by-side. As Herein, the terms "toothpaste" and "dentifrice" can be used interchangeably.

The term "water", as used herein, refers to deionized water, unless otherwise specified.

The term "water soluble" as used herein means that the material is soluble in water in the present composition. In general, the material should be soluble at 25° C. at a concentration of 0.1% by weight of the water solvent, preferably at 1%, more preferably at 5%, more preferably at 15%.

Dentifrice compositions containing a gel network phase containing a cold dispersible fatty amphiphile can be made. Examples 1 to 7, as described hereafter, have varying amounts of cold dispersible fatty amphiphiles. The cold dispersible fatty amphiphile in Examples 1-7 contains 40% cetyl alcohol, 40% stearyl alcohol, 10% sodium lauryl sulfate (SLS), and 10% sodium acrylate/sodium acryloyl dimethyl taurate copolymer. Each example was made, as described hereafter.

Examples 1-3 contain 12.50% cold dispersible fatty amphiphile (10% fatty amphiphile), 3% hydrogen peroxide, and an abrasive.

It can be especially difficult to formulate stable oral care compositions that contain peroxide because many components commonly found in oral care compositions can catalyze the hydrolysis of peroxide. When peroxide breaks down, it forms oxygen, water, and radicals. The excess gas can cause swelling and bursting of primary packaging and the radicals can cause the entire oral care composition, including the actives and flavors, to break down to a composition with a water like viscosity with decreased efficacy.

Peroxide can be incompatible with other compositions frequently found in oral care products, such as precipitated silica abrasives and certain polymers. The toothpaste composition can contain an abrasive polishing material that is compatible with peroxide. The abrasive polishing material can be selected from the group consisting of polyorganosilsesquioxane particles, calcium pyrophosphate, dicalcium phosphosphate, calcium phosphate, strontium carbonate, barium sulfate, fused silica, or combinations thereof. The abrasive polishing material is substantially free (i.e., less than 0.1 wt %, or less than 0.05 wt %, or less than 0.01 wt %, or no detectable amounts of those materials) of precipitated silica. Examples 1-2 contain 15% calcium pyrophosphate and Examples 3-4 contain polyorganosilsesquioxane particles.

The toothpaste composition can also contain a peroxide stable polymer, including but not limited to a polymer containing 2-acrylamido-2-methylpropane sulfonic acid (AMPS) polymers, copolymers and crosspolymers.

Example 4 contains 17.50% cold dispersible fatty amphiphile (14% fatty amphiphile), 5% potassium nitrate, and 15% Tospearl® 145. Tospearl® 145 (available from Momentive™ Performance Materials, New York, USA) are polyorganosilsesquioxane particles, more specifically polymethyl organosiloxane silicone resin particles, which can be incorporated into oral care products and used as an abrasive. The surface of polymethyl organosiloxane particles have methyl groups and therefore the surface contains all organic moieties that makes it hydrophobic. Thus, the particles do not absorb very much of the water that is expelled from the solid phase of the formulation and the polymethyl organosiloxane particles likely do not help with phase stability. There was no visually perceptible phase separation as determined by the Phase Separation Method for Example 4.

Example 5 contains 17.50% cold dispersible fatty amphiphile (14% fatty amphiphile), 5% potassium nitrate, and 15% Tospearl® 145. There was no visually perceptible phase separation as determined by the Phase Separation Method for Example 5.

Example 6 contains 14.50% cold dispersible fatty amphiphile (11.6% fatty amphiphile), 5% potassium nitrate, and 10% Tospearl® 145. Example 6 had no visually perceptible phase separation as determined by the Phase Separation Method. Example 6 may be consumer preferred because it can be both phase stable and has a lower level of fatty amphiphiles, which can improve the taste and mouthfeel as compared to examples with a higher level of fatty amphiphile.

Example 7, as described below, contains 6% cold dispersible fatty amphiphile (4.8% fatty amphiphile), about 0.3% iota carrageenan (iota carrageenan is commercially available from FMC Health and Nutrition (USA) and includes approximately 5% silica), 5% potassium nitrate, and 15% Zeodent® 119. Example 7 had no visually perceptible phase separation as determined by the Phase Separation Method. Example 7 may be also be preferred by consumers because it can be both phase stable, have a higher viscosity, and has a lower level of fatty amphiphiles, which can improve the taste and mouthfeel as compared to examples with a higher level of fatty amphiphiles and/or compositions without carrageenan. The carrageenan can also enhance the mouthfeel of the oral care composition.

Toothpastes that contain both gel networks which can include a cold dispersible fatty amphiphile can be enjoyed by consumers. They are used in the same manner as regular toothpaste. For instance, the American Dental Association recommends brushing at least twice a day for two minutes with a soft-bristled brush. Then the brush is placed in a user's mouth at a 45-degree angle to the gums and gently moved back and forth in short (tooth-wide) strokes. The outer surfaces, inner surfaces, and the chewing surfaces of the teeth can be brushed. A user can also brush her tongue to remove bacteria and keep her breath fresh. The toothpaste containing gel networks can be combined with other oral care regiments such as flossing, mouthwashes, whitening regimens, and regular visits to the dentist for professional cleanings and oral exams.

The user can dispense the toothpaste that contains a gel network phase from the container, which can be a metal or plastic tube. When dispensed, the first thing that a consumer may notice is the rheology of the gel network. The toothpaste can easily dispense from the container. In some examples, the toothpaste dispenses cleanly out of the container onto the brush without being stringy. The nurdle can be smooth, not lumpy, and is thick enough that it stands up on the brush without sinking into the bristles.

Next, the consumer will brush her teeth. She may find that the toothpaste feels especially smooth in her mouth and the toothpaste is not irritating. Again, she may notice that the toothpaste is not stringy, but it is easily spread throughout her entire mouth. The user may notice that the toothpaste foams. The foaming can feel unique, as it builds and/or is maintained during brushing, which can last two minutes (as recommended by the American Dental Association®) or longer. The foam is not dense and heavy, like some products that may overwhelm the consumer. Furthermore, users may notice that foam from some current commercially available toothpastes breaks down and becomes thin and watery and causes a mess during brushing, especially if the user is brushing with an electric toothbrush. However, in toothpaste that contains a gel network phase, the foam can gently build during brushing and be very pleasant. Users may also notice that the flavor pleasantly builds intensity during brushing. After expectorating the toothpaste containing a gel network, the user may find it easily removed from the sink, for instance the toothpaste can be removed by simply turning on the water for the sink. Alternatively, the toothpaste containing gel networks may not stain the sink or countertop or the user's mouth or lips.

Consumers may find that these desirable properties are maintained or substantially maintained for the entire shelf life of the product. The oral care composition may not significantly thicken during the shelf life. The actives, including the fluoride component, peroxide, and the $KNO_3$, can be relatively stable and present at effective levels at the end of the shelf life. The toothpaste can also keep the actives available so they can deliver a therapeutic effect while brushing.

After use, a consumer may find that her teeth feel especially smooth and she may notice that this smoothness lasts for hours or even throughout the entire time between brushings. It may be determined that less biofilm forms over her teeth between brushing and users of this product may have less plaque buildup over time. After using the toothpaste containing gel networks for some time (even a short period of time, such as a few brushings), a user may find that her gums are less sensitive and may have reduced bleeding. A user may also have more pleasant dental checkups because less plaque needs to be removed and her gums are not as sensitive. The user may believe that her teeth look especially white as well and/or the teeth may actually be whiter from removal of surface stains and/or intrinsic whitening. The user may have a fresh clean feeling in her mouth for an extended period of time. The user may have fresh breath for an extended period of time. The user may notice that her teeth are less sensitive.

The toothpaste can have a shelf life of at least about 1 year, alternatively at least about 1.5 years, alternatively at least about 2 years, alternatively at least about 2.5 years, and in another example at least about 3 years.

The composition can contain a cold dispersible fatty amphiphile. The composition can contain from about 1% to about 20% cold dispersible fatty amphiphile, alternatively from about 3% to about 17%, alternatively from about 5% to about 15%, alternatively from about 7% to about 13%, alternatively from about 8% to about 12%, and alternatively from about 9% to about 11.5%. The composition can contain from about 0.1% to about 5% cold dispersible fatty amphiphile, alternatively from about 0.5% to about 3%, alternatively from about 0.75% to about 2.5%, and alternatively from about 1% to about 2%. The composition can contain greater than about 0.5% cold dispersible fatty amphiphile, alternatively greater than about 1%, alternatively greater than about 3%, alternatively greater than about 5%, alternatively greater than about 7%, alternatively greater than about 8%, and alternatively greater than about 9%.

The cold dispersible fatty amphiphile can have a melting point greater than about 10° C., alternatively greater than about 25° C., alternatively greater than about 30° C., alternatively greater than about 35° C., alternatively greater than about 40° C., alternatively greater than about 45° C., alternatively greater than about 55° C. The melting point of the cold dispersible fatty amphiphile can be from about 20° C. to about 100° C., alternatively from about 30° C. to about 90° C., alternatively from about 35° C. to about 85° C., alternatively from about 40° C. to about 80° C., alternatively from about 45° C. to about 75° C., alternatively from about 50° C. to about 70° C., alternatively from about 55° C. to about 65° C., and alternatively from about 57° C. to about 67° C. Melting point can be determined by USP (United States Pharmacopeia) Testing Method <741>, Class 1a, Apparatus I.

The cold dispersible fatty amphiphile can contain straight or branched carbon chains from about C8 to about C25 and in another example from about C12 to about C22.

The cold dispersible fatty amphiphile can contain 40% cetyl alcohol, 40% stearyl alcohol, 10% sodium lauryl sulfate, and 10% sodium acrylate/sodium acryloyl dimethyl taurate co-polymer.

The cold dispersible fatty amphiphile can contain from about 40% to about 98% fatty amphiphile, alternatively from about 50% to about 95% fatty amphiphile, alternatively from about 60% to about 90% fatty amphiphile, alternatively from about 70% to about 85% fatty amphiphile, and alternatively from about 75% to about 80% fatty amphiphile. The fatty amphiphile can be a fatty alcohol. The cold dispersible fatty amphiphile can contain one fatty alcohol and/or fatty amphiphile, alternatively two different fatty alcohols and/or fatty amphiphile, alternatively three different fatty alcohols and/or fatty amphiphile, alternatively four different fatty alcohols and/or fatty amphiphiles, and alternatively five or more different fatty alcohols and/or fatty amphiphiles. The cold dispersible fatty amphiphile can contain a fatty alcohol selected from the group consisting of cetyl alcohol, stearyl alcohol, and combinations thereof. The cold dispersible fatty amphiphile can contain two fatty alcohols where the first fatty alcohol is cetyl alcohol and the second fatty alcohol is stearyl alcohol. The ratio of first fatty amphiphile to second fatty amphiphile is about 1:5 to about 5:1, alternatively from about 1:4 to about 4:1, alternatively from about 1:3 to about 3:1, alternatively from about 1:2 to about 2:1, and alternatively the ratio is about 1:1.

The cold dispersible fatty amphiphile can contain from about 1% to about 40% surfactant, alternatively from about 5% to about 30%, alternatively from about 7% to about 20%, and alternatively from about 10% to about 15%. The surfactant can be an anionic surfactant. The surfactant can be sodium lauryl sulfate.

The cold dispersible fatty amphiphile can contain from about 1% to about 40% polymer, alternatively from about 5% to about 30%, alternatively from about 7% to about 20%, in alternatively from about 8% to about 15%, alternatively from about 9% to about 14%, and alternatively from about 10% to about 12%. The polymer can be an anionic polymer. The polymer is an AMPS polymer, which can have the following structure:

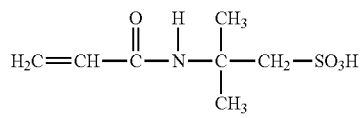

The polymer can be a polymer containing the following monomer unit:

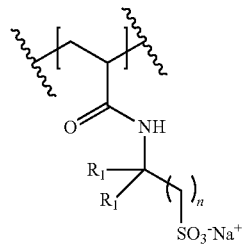

where $R_1$ is independently selected from $C_1$ to $C_4$ (lower alkyls) and n=1-3.

The ratio of surfactant to polymer in the cold dispersible fatty amphiphile is about 1:10 to about 10:1, alternatively from about 1:7 to about 7:1, alternatively from about 1:5 to about 5:1, alternatively from about 1:3 to about 3:1, and alternatively the ratio is about 1:1.

The ratio of fatty amphiphile to surfactant or polymer in the cold dispersible fatty amphiphile is 1:1 to 30:1, alternative 2:1 to 25:1, alternatively from about 3:1 to about 20:1, alternatively from about 4:1 to about 15:1, alternatively from about 5:1 to about 10:1, in alternatively from about 6:1 to about 9:1, alternatively from about 7:1 to about 8:1, and alternatively from about 8:1.

The ratio of fatty amphiphile to surfactant and polymer in the cold dispersible fatty amphiphile is 1:1 to 15:1, alternatively from about 2:1 to 10:1, alternatively from about 3:1 to about 8:1, and alternatively from about 4:1 to about 6:1, and alternatively about 4:1.

As used herein, "fatty amphiphile" refers to a compound having a hydrophobic tail group and a hydrophilic head group which does not make the compound water soluble (immiscible), wherein the compound also has a net neutral charge at the pH of the oral composition. The fatty amphiphile can be selected from the group consisting of fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxylated amines, fatty carbamates, fatty amine oxides, fatty acids, alkoxylated fatty acids, fatty diesters, fatty sorbitan esters, fatty sugar esters, methyl glucoside esters, fatty glycol esters, mono, di- and tri-glycerides, polyglycerine fatty esters, alkyl glyceryl ethers, propylene glycol fatty acid esters, cholesterol, ceramides, fatty silicone waxes, fatty glucose amides, phospholipids, and combinations thereof. Suitable fatty amphiphiles include a combination of cetyl alcohol and stearyl alcohol. The fatty amphiphile can be a fatty alcohol.

The oral care compositions may contain a fatty amphiphile. The total amount of fatty amphiphile is less than about 16%, alternatively less than about 14%, alternatively less than about 13%, alternatively less than about 12%, alternatively less than about 11%, alternatively less than about 10%, alternatively less than about 9%, alternatively less than about 7%, alternatively less than about 6%, and alternatively less than about 5%. The composition can contain a fatty amphiphile in a total amount from about 3% to about 15%, from about 5% to about 14%, alternatively from about 7% to about 13%, alternatively from about 9% to about 12%, and alternatively from about 10% to about 11.5%. The composition can contain a fatty amphiphile in a total amount from about 1% to about 10%, alternatively from about 2% to about 9%, alternatively from about 3% to about 8%, alternatively from about 4% to about 7%, and alternatively from about 4.5% to about 6%.

The oral care composition can contain one or more secondary surfactants. The secondary surfactant is typically water soluble or miscible in the solvent or oral carrier. Suitable secondary surfactants include anionic, zwitterionic, amphoteric, cationic, and nonionic secondary surfactants. Anionic secondary surfactants can contain sodium lauryl sulfate. The composition can contain a total amount of secondary surfactant from about 1% to about 15%, alternatively from about 2% to about 12%, alternatively from about 3% to about 11%, alternatively from about 4% to about 10.5%, alternatively from 5% to about 9.75%, alternatively from about 7% to about 9.5%, and alternatively from about 8% to about 9.5%. The composition can include a secondary surfactant as part of the cold dispersible fatty amphiphile and a secondary surfactant that is not part of the cold dispersible fatty amphiphile. The composition can contain 1% to 10% secondary surfactant that is not part of the cold dispersible fatty amphiphile, alternatively from about 2% to about 7%, and alternatively from about 3% to about 6%. The secondary surfactants may be a combination of more than one type of secondary surfactants, such as an anionic and nonionic secondary surfactant. Suitable solvents for the present invention can include water, edible polyhydric alcohols such as glycerin, diglycerin, triglycerin, sorbitol, xylitol, butylene glycol, erythritol, polyethylene glycol, propylene glycol, and combinations thereof.

Secondary surfactants may include anionic surfactants such as organophosphate, which include alkyl phosphates. These surface active organophosphate agents have a strong affinity for enamel surface and have sufficient surface binding propensity to desorb pellicle proteins and remain affixed to enamel surfaces. Suitable examples of organophosphate compounds include mono-, di- or triesters represented by the general structure below wherein Z1, Z2, or Z3 may be identical or different, at least one being an organic moiety, and can be selected from linear or branched, alkyl or alkenyl group of from 1 to 22 carbon atoms, optionally substituted by one or more phosphate groups; alkoxylated alkyl or alkenyl, (poly)saccharide, polyol or polyether group.

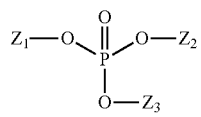

Some other organophosphate agents include alkyl or alkenyl phosphate esters represented by the following structure:

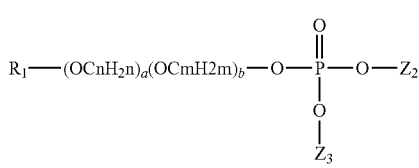

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1-(OCnH2n)a (OCmH2m)b- group. Suitable agents can include alkyl and alkyl(poly)alkoxy phosphates such as lauryl phosphate; PPGS ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. The alkyl phosphate can be polymeric. Polymeric alkyl phosphates can include those containing repeating alkoxy groups as the polymeric portion, in particular 3 or more ethoxy, propoxy isopropoxy or butoxy groups.

Zwitterionic or amphoteric secondary surfactants useful in the present invention can include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, such as carboxy, sulfonate, sulfate, phosphate or phosphonate. Suitable amphoteric secondary surfactants include betaine surfactants such as disclosed in U.S. Pat. No. 5,180,577 to Polefka et al. Typical alkyl dimethyl betaines include decyl betaine or 2-(N-decyl-N,N-dimethylammonio)acetate, coco betaine or 2-(N-coco-N, N-dimethyl ammonio)acetate, myristyl betaine, palmityl betaine, lauryl betaine, cetyl betaine, stearyl betaine, etc. Amphoteric surfactants useful herein further include amine oxide surfactants. The amidobetaines are exemplified by cocoamidoethyl betaine, cocamidopropyl betaine (CAPB), and lauramidopropyl betaine. The unwanted tastes often associated with these secondary surfactants are soapy, bitter, chemical, or artificial. The composition can contain from about 0.1% to about 6% amphoteric secondary surfactant, alternatively from about 0.5% to about 4%, alternatively from about 0.75% to about 2%, alternatively from about 1% to about 1.5%.

Additional suitable polymeric organophosphate agents can include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol)phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates. The impurities in these phosphates may induce a burning sensation. Impurities may include dodecanol, dodecanal, benzaldehyde, and other TRPA1 or TRPV1 agonists.

Cationic secondary surfactants useful in the present invention can include derivatives of quaternary ammonium compounds having one long alkyl chain containing from about 8 to 18 carbon atoms such as lauryl trimethylammonium chloride, cetyl trimethylammonium bromide, coconut alkyltrimethylammonium nitrite, cetyl pyridinium fluoride, etc. Quaternary ammonium halides having detergent properties can be used, such as those described in U.S. Pat. No.

3,535,421 to Briner et al. Certain cationic secondary surfactants can also act as germicides in the oral care compositions disclosed herein.

The oral care composition can have a viscosity from about 5 BKUs to about 70 BKUs, alternatively from about 10 BKUs to about 45 BKUs, alternatively from about 12 BKUs to about 40 BKUs, alternatively from about 15 BKUs to about 35 BKUs, alternatively from about 18 BKUs to about 30 BKUs, alternatively from about 20 BKUs to about 28 BKUs, and alternatively from about 22 BKUs to about 25 BKUs. The oral care compositions can have a viscosity from about 10 BKUs to about 200 BKUs, alternatively from about 20 BKUs to about 175 BKUs, alternatively from about 30 BKUs to about 150 BKUs, alternatively from about 50 BKUs to 100 BKUs. Viscosity can measured by the Brookfield Viscosity Test as described hereafter.

The oral care composition can have a shelf life, when stored below 40° C., of at least 6 months, alternatively at least 1 year, alternatively at least 18 months, alternatively at least 2 years, alternatively at least 30 months, and alternatively at least 3 years. The shelf life can be from about 6 months to about 5 years, alternatively from about 1 year to about 3 years, and alternatively from about 1.5 years to about 2.5 years.

The oral care composition can have a pH from about 2 to about 10, alternatively from about 4 to about 9, alternatively from about 5 to about 8, and alternatively from about 6 to about 7.5 pH can be measured using the pH Test Method as described hereafter.

Actives and other ingredients may be categorized or described herein by their cosmetic benefit, therapeutic benefit, or their postulated mode of action or function. However, it is to be understood that the active and other ingredients useful herein can, in some instances, provide more than one cosmetic benefit, therapeutic benefit, function, or can operate via more than one mode of action. Therefore, classifications herein are made for the sake of convenience and are not intended to limit an ingredient to the particularly stated function(s) or activities listed.

It is common to have a fluoride compound present in toothpastes and other oral care compositions in an amount sufficient to give a fluoride ion concentration in the composition of from about 0.0025% to about 5.0% or from about 0.005% to about 2.0%, by weight of the oral care composition to provide anticaries effectiveness. A wide variety of fluoride ion-yielding materials can be employed as sources of soluble fluoride in the present invention. Representative fluoride ion sources include: stannous fluoride, sodium fluoride, potassium fluoride, amine fluoride, sodium monofluorophosphate, indium fluoride, amine fluorides such as Olaflur, and many others. Examples of suitable fluoride ion-yielding materials are found in U.S. Pat. No. 3,535,421 to Briner et al. and U.S. Pat. No. 3,678,154 to Widder et al.

A metal salt includes zinc salts, stannous salts, potassium salts, copper salts, alkali metal bicarbonate slats, and combinations thereof. Metal salts have a wide range of functions from antimicrobial agents to sensitivity agents or buffers. The oral care compositions of the present invention may contain metal salt in an amount from about 0.05% to about 11%, from about 0.5% to about 7%, or from about 1% to about 5%, by total weight of the oral care composition. Some metal salts which may be used in the present invention, such as zinc chloride, zinc citrate, copper gluconate, and zinc gluconate, are also associated with an off taste described as dirty, dry, earthy, metallic, sour, bitter, and astringent.

Stannous salts include stannous fluoride, stannous chloride, stannous iodide, stannous chlorofluoride, stannous acetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, and combinations thereof. Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al. In addition to the stannous ion source, other ingredients used to stabilize the stannous may be included, such as the ingredients described in Majeti et al. and Prencipe et al.

Zinc salts include zinc fluoride, zinc chloride, zinc iodide, zinc chlorofluoride, zinc acetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, and combinations thereof.

Potassium salts include potassium nitrate, potassium citrate, potassium oxalate, potassium bicarbonate, potassium acetate, potassium chloride, and combinations thereof.

The copper salt can be selected from copper fluoride, copper chloride, copper iodide, copper chlorofluoride, copper acetate, copper hexafluorozirconate, copper sulfate, copper lactate, copper tartrate, copper gluconate, copper citrate, copper malate, copper glycinate, copper pyrophosphate, copper metaphosphate, copper oxalate, copper phosphate, copper carbonate, and combinations thereof. The copper salt can be selected from copper gluconate, copper acetate, copper glycinate, and combinations thereof.

Sweeteners can include saccharin, chloro-sucrose (sucralose), steviolglycosides, rebaudioside A, rebaudioside B, rebaudioside C, rebaudioside D, rebaudioside E, rebaudioside F, dulcoside A, dulcoside B, rubusoside, stevia, stevioside, acesulfame K, xylitol, neohesperidine DC, alitame, aspartame, neotame, alitame, thaumatin, cyclamate, glycyrrhizin, mogroside IV, mogroside V, Luo Han Guo sweetener, siamenoside, monatin and its salts (monatin SS, RR, RS, SR), curculin, monellin, mabinlin, brazzein, hemandulcin, phyllodulcin, glycyphyllin, phloridzin, trilobatin, baiyanoside, osladin, polypodoside A, pterocaryoside A, pterocaryoside B, mukurozioside, phlomisoside I, periandrin I, abrusoside A, cyclocarioside I,N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and combinations thereof.

Rebiana can be a steviolglycoside from Cargill Corp., Minneapolis, MN, which is an extract from the leaves of the Stevia rebaudiana plant (hereinafter referred to as "Rebiana"). This is a crystalline diterpene glycoside, about 300× sweeter than sucrose. Suitable stevioglycosides which may be combined include rebaudioside A, rebaudioside B, rebaudioside C, rebaudioside D, rebaudioside E, rebaudioside F, dulcoside A, dulcoside B, rubusoside, stevioside, or steviolbioside. According to particularly desirable examples of the present invention, the combination of high-potency sweeteners comprises rebaudioside A in combination with rebaudioside B, rebaudioside C, rebaudioside F, rebaudioside F, stevioside, steviolbioside, dulcoside A. Sweeteners are generally included in an oral care composition at a level of about 0.0005% to about 2%, by total weight of the oral care composition.

Carrier materials can include water, glycerin, sorbitol, polyethylene glycols including those having a molecular weight of less than about 50,000, propylene glycol and other edible polyhydric alcohols, ethanol, or combinations thereof. The oral care compositions of the present invention include from about 5% to about 80%, by weight of the composition, of a carrier material. The compositions can contain carrier materials in an amount of from about 10% to about 40%, by total weight of the oral care composition.

The composition can contain from about 15% to about 95% water, alternatively from about 20% to about 85%, alternatively from about 25% to about 70%, alternatively from about 28% to about 60%, alternatively from about 30% to about 50%, alternatively from about 31% to about 48%, alternatively from about 32% to about 45%, and alternatively from about 33% to about 43%. The composition can contain from about 1% to about 20% water, alternatively from about 2% to about 15% water, alternatively from about 3% to about 10% water, and alternatively from about 4% to about 8% water. The composition can contain greater than about 5% water, alternatively greater than about 8%, alternatively greater than about 10%, alternatively greater than about 15%, alternatively greater than about 20%, alternatively greater than about 25%, alternatively greater than about 30%, alternatively greater than about 40%, and alternatively greater than about 50%.

Antimicrobial agents include quaternary ammonium compounds. Those useful in the present invention include, for example, those in which one or two of the substituents on the quaternary nitrogen has a carbon chain length (typically alkyl group) from about 8 to about 20, typically from about 10 to about 18 carbon atoms while the remaining substituents (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethoylstearyl ammonium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents.

Other quaternary ammonium compounds include the pyridinium compounds. Pyridinium quaternary ammonium compounds can include bis[4-(R-amino)-1-pyridinium] alkanes as disclosed in U.S. Pat. No. 4,206,215, Jun. 3, 1980, to Bailey and cetylpyridinium and tetradecylpyridinium halide salts (i.e., chloride, bromide, fluoride and iodide).

The oral care compositions of the present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and combinations thereof. Such agents are disclosed in U.S. Pat. No. 2,946,725, Jul. 26, 1960, to Norris et al. and in U.S. Pat. No. 4,051,234 to Gieske et al. Examples of other antimicrobial agents include chlorhexidine, and flavor oils such as thymol. In another example, the antimicrobial agent can include triclosan.

Thickening material or binders may be used to provide a desirable consistency to the oral care compositions of the present invention.

Thickening materials can include carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening material to further improve texture. The thickening material can be carrageenan. Thickening materials can be used in an amount from about 0.1% to about 15%, by weight of the oral care composition. Thickening materials can be used in an amount from about 0.01% to about 3%, alternatively from about 0.1% to about 2%, alternatively from about 0.2% to about 1%, alternatively from about 0.25% to about 0.75%, alternatively from about 0.27% to about 0.5%, and alternatively from about 0.3% to about 0.4%. The oral care compositions can also contain binders that can also adjust formulation texture and mouth feel.

The thickening agent can include the addition of polymers of acrylic acid crosslinked with an unsaturated polyfunctional agent such as a polyallyl ether of sucrose. These carboxy vinyl polymers have the CTFA (Cosmetic, Toiletry and Fragrance Association) adopted name of "carbomer." A carbomer can include negatively charged polyelectrolytes, such as Carbomer 956 (available from Lubrizol Corporation, Wickliffe, Ohio). The carbomer can be selected from the group consisting of acrylates/C10-30 alkyl acrylate crosspolymer, sodium polyacrylate; polyacrylate-1 Crosspolymer (available from Lubrizol); polyacrylate Crosspolymer-11 (available from Clariant, Inc., Louisville, Kentucky, USA), acrylates/C10-30 alkyl acrylate crosspolymer, and combinations thereof. The carbomer can be Carbomer 956. The composition can contain from about 0.1% to about 15% carbomer, alternatively from about 0.3% to about 10% carbomer, alternatively from about 0.5% to about 6% carbomer, alternatively from about 0.7% to about 3% carbomer, and alternatively from about 0.9% to about 1.5% carbomer. Examples of additional carbomers can be found in U.S. Pat. No. 2,798,053.

In some oral care compositions, for instance examples that contain peroxide, it is not desirable to include certain polymers because they will not be stable. The oral care composition can be substantially free of carrageenan. The composition can be substantially free of carboxymethyl cellulose. The composition can be substantially free of xanthan gum. In The oral care composition can contain an AMPS polymer, co-polymer, and/or crosspolymer, as described above. Non-limiting examples of polymers, copolymers and crosspolymers synthesized from AMPS can include hydroxyethyl acrylate/sodium acryloyldimethyl taurate co-polymer (commercially available as Sepinov™ EMT-10 from SEPPIC S.A.), ammonium acryloyldimethyl taurate/vinyl pyrrolidone copolymer (commercially available as Aristoflex® AVC from Clariant International LTD, Muttenz, Switzerland), ammonium acryloyldimethyltaurate/beheneth-25 methacrylate crosspolymer (commercially available as Aristoflex® HMB, Clariant International LTD), sodium acrylate/sodium acryloyldimethyltaurate copolymer (a component of Sepigel EG and Simulgel SMS 88, SEPPIC S.A.), acrylamide/sodium acryloyldimethyltaurate copolymer (a component of Simulgel 600 and Simulgel 600 PHA, SEPPIC S.A.), polyacrylate crosspolymer-6 (commercially available as SepiMAX™ ZEN from SEPPIC S.A.), and combinations thereof.

The oral care composition can contain polyacrylate crosspolymer-6 (commercially available as SepiMAX™ ZEN from SEPPIC S.A., a subsidiary of the Air Liquide group, Puteaux Cedex, France). The molecular structure of polyacrylate crosspolymer-6 is shown below.

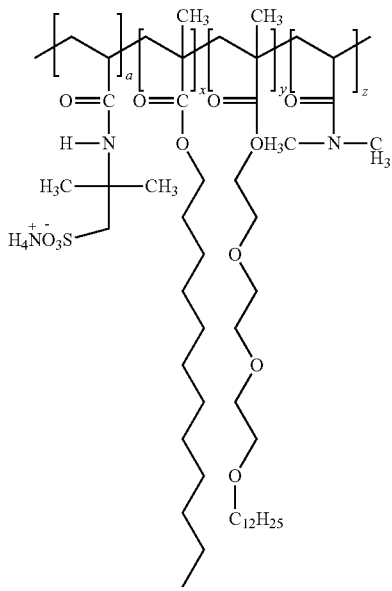

Polyacrylate crosspolymer-6 is a copolymer of Ammonium 2-methyl-24(1-oxo-2-propenyl)aminol-1-propanesulfonate, N,N, Dimethyl-2-acrylamide, Poly(oxy-1,2-ethanediyl), alpha-(2-methyl-1-oxo-2-propenyl0-omega-(dodecyloxy) and Methyl-2-propenoic acid dodecyl ester monomers.

The oral care composition can contain from about 0.1% to about 10% AMPS polymer, copolymer, or crosspolymer, alternatively from about 0.5% to about 7%, alternatively from about 1% to about 5%, alternatively from about 1.2% to about 4%, and alternatively from about 1.6% to about 3.5%. The oral care composition can contain from about 0.01% to about 5% AMPS polymer, copolymer, or crosspolymer, in another example from about 0.1% to about 3%, alternatively from about 0.25% to about 1.5%, alternatively from about 0.3% to about 1%, and alternatively from about 0.5% to about 0.8%.

The compositions of the present invention may contain antimicrobial agents in an amount of from about 0.035% or more, from about 0.1% to about 2.0%, from about 0.045% to about 1.0%, or from about 0.05% to about 0.10%, by total weight of the oral care composition. Alternatively from about 0.001% to about 1.5% antimicrobial agent, alternatively from about 0.005% to about 0.8%, alternatively from 0.01% to about 0.7%, alternatively from about 0.05% to about 0.5%, and alternatively from about 0.1% to about 0.3%.

Non-limiting examples of peroxide (peroxygen) compounds can include hydrogen peroxide, urea peroxide, calcium peroxide, sodium peroxide, zinc peroxide, polyvinylpyrrolidone peroxide complex or combinations thereof. The composition can contain greater than about 0.05% peroxide, alternatively greater than about 0.5% peroxide, alternatively greater than about 0.75%, alternatively greater than about 1%, alternatively greater than about 1.25%, alternatively greater than about 1.5%, alternatively greater than about 1.75%, alternatively greater than about 2%, alternatively greater than about 2.25%, alternatively greater than about 2.5%, alternatively greater than about 2.75%, alternatively greater than about 2.85%, i alternatively greater than about 2.9%, alternatively greater than about 2.95%, alternatively greater than about 3%, alternatively greater than about 4%, alternatively greater than about 5%, and alternatively greater than about 6%. The composition can contain from about 0.01% to 10% peroxide, alternatively from about 0.05% to about 8%, alternatively from about 0.1% to about 5%, alternatively 0.5% to about 4.5%, alternatively 1% to about 4%, alternatively about 1.5% to about 3.5%, and alternatively about 2% to about 3%. The composition can contain from about 1% to about 10% peroxide, alternatively from about 2% to about 8% peroxide, alternatively from about 3% to about 7% peroxide, and alternatively from about 4% to about 6% peroxide. The composition can contain from about 0.01% to about 6% peroxide, alternatively from about 0.05% to about 3%, and alternatively from about 0.1% to about 1%.

The composition can be free of or substantially free of a peroxide component.

The oral care composition can include bleaching agents. Bleaching agents can include perborates, percarbonates, peroxyacids, persulfates, and combinations thereof. One example of a percarbonate is sodium percarbonate. An example of a persulfate includes oxones. Some bleaching agents provide a burn sensation within an oral care composition, for example peroxides and percarbonates.

The compositions of the present invention may contain bleaching agents in an amount of from about 0.01% to about 30%, from about 0.1% to about 10%, or from about 0.5% to about 5%, by total weight of the oral care composition.

Flavors that may be used in the oral care compositions can include mint oils, and components thereof, wintergreen, clove bud oil, cassia, sage, parsley oil, marjoram, lemon, orange, propenyl guaethol, heliotropine, cis-4-heptenal, diacetyl, methyl-ρ-tert-butyl phenyl acetate, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, neral, geranial, geraniol nerol, maltol, ethyl maltol, anethole, dihydroanethole, carvone, menthone, β-damascenone, ionone, γ-decalactone, γ-nonalactone, γ-undecalactone, isopulegol, piperitone, or combinations thereof. Generally suitable flavoring ingredients are chemicals with structural features and functional groups that are less prone to redox reactions. These include derivatives of flavor chemicals that are saturated or contain stable aromatic rings or ester groups.

Flavors can be present in an amount of from about 0.4% to about 5%, by total weight of the oral care composition, alternatively from about 0.8% to about 4%, alternatively from about 1% to about 3.5%, and alternatively from about 1.5% to about 3%. It can be desirable to have a flavor composition at less than about 4%, by weight of the oral care composition, alternatively less than about 3.5%, alternatively less than about 3%, and alternatively less than about 2%.

Dentifrice compositions of the present invention may also comprise an anti-calculus agent, which may be present from about 0.05% to about 50%, by weight of the dentifrice composition, alternatively from about 0.05% to about 25%, and alternatively from about 0.1% to about 15%. The compositions can contain an amount of anti-calculus agent that is effective in tartar control effective. The amount of pyrophosphate salt may be from about 1.5% to about 15%, alternatively from about 2% to about 10%, or alternatively from about 3% to about 8%. The anti-calculus agent may be selected from the group consisting of polyphosphates (including pyrophosphates) and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof. The salts can be alkali metal salts. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium)tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. The composition can contain from about 1% to about 30% polyphosphate salts, alternatively from about 5% to about 25%, alternatively from about 10% to about 20%, alternatively from about 11% to about 15%, and alternatively about 13%. Polyphosphates larger than tetrapolyphosphate usually occur as amorphous glassy materials. In one embodiment the polyphosphates are those manufactured by FMC Corporation, which are commercially known as Sodaphos (n≈6), Hexaphos (n≈13), and Glass H (n≈21, sodium hexametaphosphate), and mixtures thereof. The pyrophosphate salts useful in the present invention include, alkali metal pyrophosphates, di-, tri-, and mono-potassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof, azacyclohexane-2,2-diphosphonic acid, azacyclopentane-2,2-diphosphonic acid, N-methyl-azacyclopentane-2,3-diphosphonic acid, EHDP (ethane-1-hydroxy-1,1,-diphosphonic acid), AHP (azacycloheptane-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

Examples of some colorants that may be used in oral care compositions include D&C Yellow No. 10, FD&C Blue No. 1, FD&C Red No. 40, D&C Red No. 33 and combinations thereof. In certain examples, the composition comprises colorant in an amount of from about 0.0001% to about 0.1% or from about 0.001% to about 0.01%, by weight of the oral care composition. Some colorants provide an unwanted taste, for example, D&C Red No. 33. The unwanted tastes often associated with this colorant are metallic, sharp, or chemical. Colorants are generally present in an amount of from about 0.001% to about 0.5%, by weight of the oral care composition.

Sensates may also be part of an oral care composition. Sensate molecules such as cooling, warming, and tingling agents are useful to deliver signals to the user. Sensates are generally present in an amount of from about 0.001% to about 2%, by weight of the oral care composition. The most well-known cooling sensate compound can be menthol, particularly L-menthol, which is found naturally in peppermint and spearmint oils notably of Mentha piperita, Mentha arvensis L and Mentha viridis L. Other isomers of menthol (neomenthol, isomenthol and neoisomenthol) have somewhat similar, but not identical odor and taste, for instance having disagreeable odor and taste described as earthy, camphor, musty, etc. The biggest difference among the isomers is in their cooling potency. L-menthol provides the most potent cooling, by having the lowest cooling threshold of about 800 ppb, which is the concentration level where the cooling effect can be clearly recognized. At this level, there can be no cooling effect for the other isomers. For example, d-neomenthol is reported to have a cooling threshold of about 25,000 ppb and 1-neomenthol about 3,000 ppb.

Of the menthol isomers the 1-isomer occurs most widely in nature and is typically what is referred by the name menthol having coolant properties. L-menthol has the characteristic peppermint odor, has a clean fresh taste and exerts a cooling sensation when applied to the skin and mucosal surfaces.

Among synthetic coolants, many are derivatives of or are structurally related to menthol, for example containing the cyclohexane moiety, and derivatized with functional groups including carboxamide, ketal, ester, ether and alcohol. Examples include the ρ-menthanecarboxamide compounds such as N-ethyl-ρ-menthan-3-carboxamide, known commercially as "WS-3", and others in the series such as WS-5 (N-ethoxycarbonylmethyl-ρ-menthan-3-carboxamide), WS-12 (1R*,2S*)—N-(4-Methoxyphenyl)-5-methyl-2-(1-methylethyl)cyclohexanecarboxamide] and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D) all available from Takasago Corp., Tokyo, Japan; menthone glycerol acetal known as MGA; menthyl esters such as menthyl acetate, menthyl acetoacetate, menthyl lactate known as Frescolat® supplied by Symrise AG, Holzminden, Germany, and monomenthyl succinate under the tradename Physcool from V. Mane FILS, Notre Dame, France. TK-10 is described in U.S. Pat. No. 4,459,425 to Amano et al. Other alcohol and ether derivatives of menthol are described in GB 1,315,626 and in U.S. Pat. Nos. 4,029,759; 5,608,119; and 6,956,139. WS-3 and other carboxamide cooling agents are described in U.S. Pat. Nos. 4,136,163; 4,150,052; 4,153,679; 4,157,384; 4,178,459 and 4,230,688.

Additional N-substituted ρ-menthane carboxamides are described in WO 2005/0495551 including N-(4-cyanomethylphenyl)-ρ-menthanecarboxamide, N-(4-sulfamoylphenyl)-ρ-menthanecarboxamide, N-(4-cyanophenyl)ρ-menthanecarboxamide, N-(4-acetylphenyl)-ρ- menthanecarboxamide, N-(4-hydroxymethylphenyl)-ρ-menthanecarboxamide and N-(3-hydroxy-4-methoxyphenyl)-ρ-menthanecarboxamide Other N-substituted ρ-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,917,613; 3,991,178; 5,703,123; 5,725,865; 5,843,466; 6,365,215; and 6,884,903. Ketal derivatives are described, e.g., in U.S. Pat. Nos. 5,266,592; 5,977,166; and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112. Reviews on the coolant activity of menthol and synthetic coolants include H. R. Watson, et al. J. Soc. Cosmet. Chem. (1978), 29, 185-200 and R. Eccles, J. Pharm. Pharmacol., (1994), 46, 618-630 and phosphine oxides as reported in U.S. Pat. No. 4,070,496.

Warming sensates can include ethanol; capsicum; nicotinate esters, such as benzyl nicotinate; polyhydric alcohols; capsicum powder; a capsicum tincture; capsicum extract; capsaicin; homocapsaicin; homodihydrocapsaicin; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof. Warming sensates are generally included in an oral care composition at a level of about 0.05% to about 2%, by weight of the oral care composition.

Abrasive polishing material can be any material that does not excessively abrade dentin. The oral care compositions of the present invention may comprise abrasive polishing material in an amount of from about 6% to about 70% or from about 10% to about 50%, by weight of the oral care composition. The composition can contain from about 2% to about 25% abrasive polishing material, alternatively from about 5% to about 20%, alternatively from about 7% to about 18%, alternatively from about 9% to about 16%, and alternatively from about 12% to about 15%. The composition can contain 10% abrasive polishing material and alternatively about 15% abrasive polishing material.

The abrasive polishing material can have a BET surface area greater than about 5 $m^2/g$, alternatively greater than about 10 $m^2/g$, alternatively greater than about 15 $m^2/g$, alternatively greater than about 18 $m^2/g$, alternatively greater than about 25 $m^2/g$, alternatively greater than about 30 $m^2/g$, alternatively greater than about 35 $m^2/g$, alternatively greater than about 40 $m^2/g$, and alternatively greater than about 50 $m^2/g$. The BET surface area of the abrasive polishing material is from about 5 $m^2/g$ to about 30 $m^2/g$, alternatively from about 10 $m^2/g$ to about 200 $m^2/g$, alternatively from about 20 $m^2/g$ to about 150 $m^2/g$, alternatively from about 25 $m^2/g$ to about 100 $m^2/g$, alternatively from about 30 $m^2/g$ to about 75 $m^2/g$, alternatively from about 35 $m^2/g$ to about 60 $m^2/g$, alternatively from about 38 $m^2/g$ to about 50 $m^2/g$, and alternatively from about 40 $m^2/g$ to about 45 $m^2/g$. The precipitated silica can have a BET surface area from about 19 $m^2/g$ to about 55 $m^2/g$ and alternatively from about 19 $m^2/g$ to about 35 $m^2/g$. The silica can have a BET surface area from about 10 $m^2/g$ to about 80 $m^2/g$, alternatively from about 20 $m^2/g$ to about 70 $m^2/g$, alternatively from about 25 $m^2/g$ to about 50 $m^2/g$, or alternatively from about 30 $m^2/g$ to about 45 $m^2/g$. BET surface area is determined by BET nitrogen absorption method of Brunaur et al., *J. Am. Chem. Soc.,* 60, 309 (1938). See also U.S. Pat. No. 7,255,852 to Gallis.

The abrasive polishing material has a LOD of about 1% to about 10%, alternatively from about 3% to about 7%, alternatively from about 4% to about 6.75%, and alternatively from about 5.6% to about 6.1%. The LOD can be less than about 7%, alternatively less than about 6.5%, and alternatively less than about 6.25%. The abrasive polishing material can have an LOI from about 2% to about 10%, alternatively from about 3% to about 7%, alternatively from about 4% to about 6%, and alternatively from about 5.1%. The LOI can be greater than about 3%, alternatively greater than about 4%, and alternatively greater than about 5%. The sum of LOD and LOI can be from about 5% to about 20%, alternatively from about 7% to about 17%, alternatively from about 8% to about 15%, alternatively from about 9% to about 14%, and alternatively from about 10% to about 12.5%. Silicas with less than about 5% bound and free water may be considered substantially non-hydrated. The total bound and free water can be calculated by totaling two measurements, loss on drying (LOD) and loss on ignition (LOI). For loss on drying, performed first, a sample may be dried at 105° C. for two hours, the weight loss being the free water. For loss on ignition, the dried sample then may be heated for one hour at 1000° C., the weight loss being the bound water. The sum of the LOD and LOI represents the total bound and free water in the original sample.

Typical abrasive polishing materials can include silicas including gels and precipitates; aluminas; phosphates including orthophosphates, polymetaphosphates, and pyrophosphates; and mixtures thereof. Specific examples include silicone microspheres such as polyorganosilsesquioxane particles, dicalcium orthophosphate dihydrate, calcium pyrophosphate, tricalcium phosphate, calcium polymetaphosphate, insoluble sodium polymetaphosphate, rice hull silica, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510. In certain examples, if the oral composition or particular phase comprises a polyphosphate having an average chain length of about 4 or more, calcium containing abrasives and alumina are not preferred abrasives. In certain examples, the composition is substantially free of silica.

The composition can contain a silica abrasive. Silica abrasive polishing materials that may be used in the present invention, as well as other abrasives, generally have an average particle size ranging between about 0.1 to about 30 μm or from about 5 to about 15 μm. The abrasive can be precipitated silica or silica gels such as the silica xerogels described in Pader et al., U.S. Pat. No. 3,538,230 and DiGiulio, U.S. Pat. No. 3,862,307. Silica xerogels marketed under the trade name "Syloid" by the W.R. Grace & Company, Davison Chemical Division, Augusta, Georgia may be used. Also precipitated silica materials such as those marketed by the J. M. Huber Corporation, Edison, NJ under the trade name, "Zeodent", particularly the silica carrying the designation "Zeodent 119", may be used. The types of silica dental abrasives useful in the oral care compositions of the present invention are described in more detail in U.S. Pat. Nos. 4,340,583; 5,589,160; 5,603,920; 5,651,958; 5,658,553; and 5,716,601.

The abrasive can include polymethyl organosiloxane particles. The types of polymethyl organosiloxane particles useful in the oral care compositions of the present invention are described in more detail in U.S. Pat. No. 9,017,647. It may be advantageous to select an abrasive containing polymethyl organosiloxane particles because they are less reactive with ingredients commonly found in oral care compositions, in including oral care actives.

The abrasive can include calcium pyrophosphate. The abrasive can include poly(methyl methacrylate), calcium carbonate, dicalcium phosphate, and/or barium sulfate.

Humectants keep oral care compositions from hardening upon exposure to air and certain humectants can also impart desirable sweetness of flavor to dentifrice compositions. Suitable humectants for use in the present invention include glycerin, sorbitol, polyethylene glycol, propylene glycol, xylitol, and other edible polyhydric alcohols. The oral care compositions of the present invention may comprise humectants in an amount of from about 0% to about 70% or from about 15% to about 55%, by weight of the oral care composition.

Brookfield Viscosity Test

The viscometer is Brookfield viscometer, Model ½ RVT, with a Brookfield "Heliopath" stand (available from Brookfield Engineering Laboratories, Middleboro, Massachusetts). The spindle is a conventional "E-series" T-shaped spindle. The viscometer is placed on the Heliopath stand and leveled via spirit levels. The E spindle is attached, and the viscometer is set to 2.5 RPM while it is running. The viscosity is measured after 1 minute and the temperature is constant at 25° C. The "Brookfield Unit" in which results obtained from this method have traditionally been expressed is simply the direct readout of the instrument under standard conditions, i.e., using the "E" spindle at 2.5 RPM, or calculated equivalent.

pH Test Method

First, calibrate the Thermo Scientific Orion 320 pH meter. Do this by turning on the pH meter and waiting for 30 seconds. Then take the electrode out of the storage solution, rinse the electrode with distilled water, and carefully wipe the electrode with a scientific cleaning wipe, such as a Kimwipe®. Submerse the electrode in the pH 7 buffer and press the calibrate button. Wait until the pH icon stops flashing and press the calibrate button a second time. Rinse the electrode with distilled water and carefully wipe the electrode with a scientific cleaning wipe. Then submerse the electrode into the pH 4 buffer and wait until the pH icon stops flashing and press the measure button. Rinse the electrode with distilled water and carefully wipe with a scientific cleaning wipe. Now the pH meter is calibrated and can be used to test the pH of a solution.

The pH of the liquid medication is measured using the calibrated pH meter at ambient temperature.

Phase Separation Method

After the toothpaste is made, 25 grams of the composition is placed in a polypropylene speed mix jar (max 40 Speed-Mixer™ contain available from FlackTek™ Inc.) with a screwed lid screwed hand tight. Then, the container is placed in an oven (Espec™ LHV-113 Temperature and Humidity Cabinet was used here) at 40° C. for about 8 hours. Then, the container is removed and it is observed to see if any phase separation was visually perceptible.

EXAMPLES

| | Ex. 1 (wt. %) | Ex. 2 (wt. %) | Ex. 3 (wt. %) | Ex. 4 (wt. %) | Ex. 5 (wt. %) | Ex. 6 (wt. %) | Ex. 7 (wt. %) |
|---|---|---|---|---|---|---|---|
| Water | 56.68 | 55.48 | 57.20 | 11.50 | 9.28 | 16.72 | 16.47 |
| Cold Dispersible Fatty Amphiphile[1] | 12.50 | 12.50 | 12.50 | 17.50 | 17.50 | 14.50 | 6.00 |
| Iota Carrageenan[2] | — | — | — | — | — | — | 0.300 |
| Sorbitol Solution USP[3] | — | — | — | 29.96 | 30.04 | 30.57 | 41.10 |
| Saccharin Sodium USP Granular, High Moisture[4] | — | — | — | 0.45 | 0.45 | 0.45 | 0.45 |
| Potassium Nitrate USP | — | — | — | 5.00 | 5.00 | 5.00 | 5.00 |
| Sodium Fluoride | — | — | 0.24 | 0.24 | 0.24 | 0.24 | 0.24 |
| Calcium Pyrophosphate | 15.00 | 15.00 | — | — | — | — | — |
| Tospearl ® 145[5] | — | — | 15.00 | 15.00 | 15.00 | 10.00 | — |
| Zeodent ® 119[6] | — | — | — | — | — | — | 15.00 |
| Sodium Monofluorophosphate | 0.760 | 0.760 | — | — | — | — | — |
| Sodium Acid Pyrophosphate | 0.80 | 0.30 | 0.80 | 0.094 | 0.090 | 0.11 | — |
| Disodium phosphate | 0.20 | 0.20 | 0.20 | — | — | — | — |
| Disodium phosphate (heptahydrate) | — | 0.68 | — | — | — | — | — |
| Monosodium phosphate (monohydrate) | — | 0.02 | — | — | — | — | — |
| Tetrasodium Pyrophosphate | — | 1.00 | — | — | — | — | — |
| Sucralose | 0.50 | 0.50 | — | 0.25 | 0.25 | 0.25 | 0.25 |

-continued

|  | Ex. 1 (wt. %) | Ex. 2 (wt. %) | Ex. 3 (wt. %) | Ex. 4 (wt. %) | Ex. 5 (wt. %) | Ex. 6 (wt. %) | Ex. 7 (wt. %) |
|---|---|---|---|---|---|---|---|
| Hydrogen Peroxide (35% Ultra Cosmetic) | 8.57 | 8.57 | 8.57 | — | — | — | — |
| Flavor | 2.91 | 2.91 | 2.91 | 2.15 | 2.15 | 2.15 | 1.74 |
| Sodium Lauryl Sulfate Solid | 2.08 | 2.08 | 2.08 | — | — | — | — |
| Sodium Lauryl Sulfate Solution (29%) | — | — | — | 17.857 | 20.000 | 20.000 | 9.50 |
| Cocamidopropyle Betaine Solution (30%) | — | — | — | — | — | — | 3.75 |
| Sodium Hydroxide Solution (50%) Food Chemical Codex | — | — | — | — | — | — | 0.20 |

[1] The cold dispersible fatty amphiphile is 40% cetyl alcohol, 40% stearyl alcohol, 10% sodium lauryl sulfate, and 10% sodium acrylates/sodium acryloyl dimethyl taurate copolymer.
[2] Iota Carrageenan contains approximately 5% silica as a processing aid (commercially available from FMC Health and Nutrition (USA))
[3] Sorbitol Solution USP is an aqueous solution containing 70% sorbitol
[4] Saccharin Sodium USP Granular, high moisture contains up to 14% water
[5] Polymethyl organosiloxane particles, more specifically polymethyl organosiloxane silicone resin particles, available from Momentive™ Performance Materials, New York
[6] Available from J. M. Huber Corporation, Edison, New Jersey Examples 1-3 were made using the following procedure. A jacketed mix tank was set to 30° C. and water was added to the vessel. Then, the cold dispersible fatty amphiphile was added with homogenization. Then, the lid was closed and the mixture was agitated and homogenized. Then, the following materials (if present) were added to the vessel: sucralose, disodium phosphate, sodium phosphate (heptahydrate), sodium phosphate (monohydrate), sodium acid pyrophosphate, tetrasodium pyrophosphate, sodium monofluorophosphate, and sodium fluoride were added with agitation and homogenization. Then, the abrasive (calcium pyrophosphate or Tospearl® 145) was added to the vessel with agitation. Once the abrasive had wetted out, the mixture was deaerated. Once the composition was approximately homogenous and approximately all of the air was removed, the hydrogen peroxide was added with homogenization and the remaining SLS and flavor were added with agitation. The mixture was then deaerated again. Finally, the first bit of heterogeneous material was removed at the beginning of pumping out of mix tank into a separate container and was discarded as scrap. Once the material began to appear homogeneous, it was collected in a clean container and stored as the final composition. The final composition can then be used to fill tubes, if desired.

Examples 4-7 were made as follows. A jacketed mix tank was set to 30° C. The water, 0.1% SLS, and sorbitol solution were added to the vessel with homogenization. Then, the carrageenan (if present) was slowly added and then the cold dispersible fatty amphiphile was added under agitation to form a substantially homogenous mixture. Then, the following materials were added to the vessel: saccharine, sucralose, sodium fluoride, sodium acid pyrophosphate, and potassium nitrate with agitation and homogenization. Then, the abrasive (Tosperal® 145 or Zeodent® 119) was added to the vessel with agitation. Once the abrasive had wetted out, the mixture was deaerated. Once the composition was approximately homogenous and approximately all of the air was removed, the remaining SLS, cocamidopropyle betaine solution (if present), and flavor were added to the vessel with agitation. The mixture was then deaerated again. Next, a sample was removed and the pH was measured. In examples where pH adjustment was needed sodium hydroxide solution was added until the composition reached the target pH and the mixture was deaerated again. Finally, the first bit of heterogeneous material was removed at the beginning of pumping out of mix tank into a separate container and was discarded as scrap. Once the material began to appear homogeneous, it was collected in a clean container and stored as the final composition. The final composition can then be used to fill tubes, if desired.

Combinations

A. An oral care composition comprising: (a) a gel network phase comprising from about 1% to about 20% cold dispersible fatty amphiphile, or from about 3% to about 17% cold dispersible fatty amphiphile, or from about 5% to about 15% cold dispersible fatty amphiphile; (b) from about 2% to about 25% abrasive, or from about 5% to about 20% abrasive, or from about 7% to about 18% abrasive, or from about 9% to about 16% abrasive; (c) and a fluoride ion source selected from the group consisting of stannous fluoride, sodium fluoride, potassium fluoride, amine fluoride, sodium monofluorophosphate, indium fluoride, amine fluoride, and combinations thereof; wherein the oral care composition comprises from about 3% to about 17% fatty amphiphile, or from about 5% to about 15% fatty amphiphile, or from about 7% to about 13% fatty amphiphile, or from about 10% to about 11.5% fatty amphiphile; wherein phase separation is not visually perceptible as determined by the phase separation method.

B. An oral care composition comprising: (a) a gel network phase comprising a cold dispersible fatty amphiphile; (b) from about 0.01% to about 3% thickening material, or from about 0.1% to about 2% thickening material, or from about 0.2% to about 1% thickening material, or from about 0.27% to about 0.5% thickening material wherein the thickening material is selected from the group consisting of carboxyvinyl polymers, carrageenan, hydroxyethyl cellulose, water soluble salts of cellulose ethers, gum karaya, xanthan gum, gum arabic, gum tragacanth, magnesium aluminum silicate, finely divided silica, and combinations thereof; (c) an abrasive; and (d) and a fluoride ion source selected from the group consisting of stannous fluoride, sodium fluoride, potassium fluoride, amine fluoride, sodium monofluorophosphate, indium fluoride, amine fluorides, and combinations thereof; wherein the oral care composition comprises less than about 16% fatty amphiphile, or less than about 14% fatty amphiphile, or less than about 13% fatty amphiphile, or less than about than about 10% fatty amphiphile, or less than about 7% fatty amphiphile, or less than about 6% fatty amphiphile; and wherein phase separation is not visually perceptible as determined by the phase separation method.

C. The oral care composition according to paragraph A or B wherein the cold dispersible fatty amphiphile comprises: (a) from about 50% to about 95% fatty amphiphile, or from about 60% to about 90% fatty amphiphile, or from about 70% to about 85% fatty amphiphile; (b) from about 1% to about 40% surfactant, or from about 5% to about 30% surfactant, or from about 7% to about 20% surfactant; (c) from about 1% to about 30% polymer, or from about 5% to about 20% polymer, or from about 9% to about 14% polymer, or from about 10% to about 12% polymer.

D. The oral dosage form according to any one of the preceding paragraphs A-C wherein the cold dispersible fatty amphiphile comprises one or more straight or branched carbon chains from about C8 to about C25, or from about C12 to about C22.

E. The oral care composition any one of the preceding paragraphs A-D wherein the cold dispersible fatty amphiphile comprises 40% cetyl alcohol, 40% stearyl alcohol, 10% sodium lauryl sulfate, and 10% sodium acrylate/sodium acryloyl dimethyl taurate co-polymer.

F. The oral care composition any one of the preceding paragraphs A-E wherein the abrasive comprises precipitated silica.

G. The oral care composition according to paragraph F wherein the precipitated silica has a BET surface area from about 19 m$^2$/g to about 55 m$^2$/g.

H. The oral care composition according to paragraph A-G wherein the fatty amphiphile comprises a fatty alcohol selected from the group consisting of cetyl alcohol, stearyl alcohol, and combinations thereof.

I. The oral care composition according to any one of the preceding paragraphs A-H wherein the composition has a viscosity from about 5 BKUs to about 70 BKUs, or from about 10 BKUs to about 45 BKUs, or from about 15 BKUs to about 35 BKUs, or from about 18 BKUs to about 30 BKUs.

J. The composition according to any one of the preceding paragraphs A-I wherein the composition further comprises from about 15% to about 95% water, or from about 25% to about 70% water, or from about 30% to about 50% water, or from about 32% to about 45% water.

K. The oral care composition according to any one of the preceding paragraphs A-J wherein the cold dispersible fatty amphiphile comprises: (a) a fatty amphiphile; (b) a surfactant; and (c) a 2-acrylamido-2-methylpropane sulfonic acid (AMPS) polymer; wherein the weight ratio of fatty amphiphile to surfactant is from about 2:1 to 25:1, or from about 4:1 to about 15:1, or from about 6:1 to about 9:1.

L. The oral care composition according to any one of the preceding paragraphs A-K wherein the thickening material comprises carrageenan.

M. The oral care composition according to paragraph L wherein the composition comprises from about 0.1% to about 1% carrageenan.

N. The oral care composition according to paragraphs A-M wherein the composition further comprises a peroxide compounded selected from the group consisting of hydrogen peroxide, urea peroxide, calcium peroxide, sodium peroxide, zinc peroxide, polyvinylpyrrolidone peroxide complex or combinations thereof.

O. The oral care composition according to paragraph N wherein the composition comprises from about 0.01% to about 6% peroxide, or from about 0.05% to about 3% peroxide, or from about 0.1% to about 1% peroxide.

P. A method for making an oral care composition comprising the steps of: (a) combining water and a cold dispersible fatty amphiphile; (b) adding a fluoride ion source and/or an abrasive; (c) adding secondary surfactant; (d) mixing until the composition is substantially homogeneous; (e) deaerating until the composition is substantially free of air; wherein a gel network is formed and wherein the composition is not heated above 30° C.

Q. The oral care composition of paragraph P wherein the cold dispersible fatty amphiphile has a melting point greater than about 25° C.

Values disclosed herein as ends of ranges are not to be understood as being strictly limited to the exact numerical values recited. Instead, unless otherwise specified, each numerical range is intended to mean both the recited values and any real numbers including integers within the range. For example, a range disclosed as "1 to 10" is intended to mean "1, 2, 3, 4, 5, 6, 7, 8, 9, and 10" and a range disclosed as "1 to 2" is intended to mean "1.1, 1.2, 1.3, 1.4, 1.5, 1.6, 1.7, 1.8, 1.9, and 2."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an oral care composition comprising the steps of:
   a. combining water and a cold dispersible fatty amphiphile, wherein the cold dispersible fatty amphiphile comprises:
      (i) about 40%, by weight of the cold dispersible fatty amphiphile, of cetyl alcohol;
      (ii) about 40%, by weight of the cold dispersible fatty amphiphile, of stearyl alcohol;
      (iii) about 10%, by weight of the cold dispersible fatty amphiphile, of an anionic surfactant; and
      (iv) about 10%, by weight of the cold dispersible fatty amphiphile, of a sodium acrylate/sodium acryloyl dimethyl taurate co-polymer;
   b. adding a fluoride ion source, an abrasive, a metal salt, a peroxide source, or combinations thereof;
   c. adding a secondary surfactant;
   d. mixing until the composition is homogeneous; and
   e. deaerating until the composition is free of air;
   wherein a gel network is formed and the composition is not heated above 30° C. during any portion of the method.

2. The method of claim 1, wherein the fluoride ion source is added and comprises stannous fluoride, sodium fluoride, potassium fluoride, amine fluoride, sodium monofluorophosphate, indium fluoride, amine fluoride, or combinations thereof.

3. The method of claim 1, wherein the abrasive is added and comprises polyorganosilsequioxane particles, calcium pyrophosphate, dicalcium phosphate, calcium phosphate, strontium carbonate, barium sulfate, fused silica, or combinations thereof.

4. The method of claim 1, wherein the peroxide source is added and comprises hydrogen peroxide, urea peroxide, calcium peroxide, sodium peroxide, zinc peroxide, polyvinylpyrrolidone peroxide complex, or combinations thereof.

5. The method of claim 1, wherein the metal salt is added and comprises a zinc salt, a stannous salt, a potassium salt, a copper salt, an alkali metal bicarbonate salt, or combinations thereof.

6. The method of claim 5, wherein the metal salt comprises the potassium salt, and the potassium salt comprises potassium nitrate.

7. The method of claim 1, wherein the oral care composition has a viscosity from about 10 BKUs to about 45 BKUs.

8. The method of claim 1, wherein the oral care composition further comprises from about 25% to about 70%, by weight of the composition, of water.

9. An oral care composition prepared by a process comprising the steps of:
   a. combining water and a cold dispersible fatty amphiphile, wherein the cold dispersible fatty amphiphile comprises:
      (i) about 40%, by weight of the cold dispersible fatty amphiphile, of cetyl alcohol;
      (ii) about 40%, by weight of the cold dispersible fatty amphiphile, of stearyl alcohol;
      (iii) about 10%, by weight of the cold dispersible fatty amphiphile, of an anionic surfactant; and
      (iv) about 10%, by weight of the cold dispersible fatty amphiphile, of a sodium acrylate/sodium acryloyl dimethyl taurate co-polymer;
   b. adding a fluoride ion source, an abrasive, a metal salt, a peroxide source, or combinations thereof;
   c. adding a secondary surfactant;
   d. mixing until the composition is homogeneous; and
   e. deaerating until the composition is free of air;
   wherein a gel network is formed and the composition is not heated above 30° C. during any portion of the method.

10. The oral care composition of claim 9, wherein the fluoride ion source is added and comprises stannous fluoride, sodium fluoride, potassium fluoride, amine fluoride, sodium monofluorophosphate, indium fluoride, amine fluoride, or combinations thereof.

11. The oral care composition of claim 9, wherein the abrasive is added and comprises polyorganosilsequioxane particles, calcium pyrophosphate, dicalcium phosphate, calcium phosphate, strontium carbonate, barium sulfate, fused silica, or combinations thereof.

12. The oral care composition of claim 9, wherein the peroxide source is added and comprises hydrogen peroxide, urea peroxide, calcium peroxide, sodium peroxide, zinc peroxide, polyvinylpyrrolidone peroxide complex, or combinations thereof.

13. The oral care composition of claim 9, wherein the metal salt is added and comprises a zinc salt, a stannous salt, a potassium salt, a copper salt, an alkali metal bicarbonate salt, or combinations thereof.

14. The oral care composition of claim 13, wherein the metal salt comprises the potassium salt, and the potassium salt comprises potassium nitrate.

15. The oral care composition of claim 9, wherein the oral care composition has a viscosity from about 10 BKUs to about 45 BKUs.

16. The oral care composition of claim 9, wherein the oral care composition further comprises from about 25% to about 70%, by weight of the composition, of water.

* * * * *